United States Patent
Schmid-Schoenbein et al.

(10) Patent No.: US 6,534,283 B1
(45) Date of Patent: Mar. 18, 2003

(54) METHOD FOR TREATMENT AND PREVENTION OF PHYSIOLOGICAL SHOCK

(75) Inventors: Geert Schmid-Schoenbein, Del Mar, CA (US); Tony Hugli, San Diego, CA (US); Hiroshi Mitsuoka, Hamamatsu (JP)

(73) Assignees: The Regents of the University of California, Oakland, CA (US); The Scripps Institute, La Jolla, CA (US)

( * ) Notice: Subject to any disclaimer, the term of this patent is extended or adjusted under 35 U.S.C. 154(b) by 0 days.

(21) Appl. No.: 09/718,783

(22) Filed: Nov. 22, 2000

Related U.S. Application Data

(60) Provisional application No. 60/167,311, filed on Nov. 24, 1999.

(51) Int. Cl.[7] ........................... C12Q 1/37; A61K 38/05; C07K 5/06
(52) U.S. Cl. ........................... 435/23; 435/24; 435/213; 514/2; 514/18; 514/19; 514/12; 530/330; 530/331; 530/350; 560/34; 560/35; 560/36
(58) Field of Search ........................... 435/23, 24, 213; 514/2, 12, 18, 19, 539; 530/350, 331, 330; 560/34, 35, 36

(56) References Cited

U.S. PATENT DOCUMENTS 5,412,073 A  5/1995  Kalsheker ................. 530/350
6,001,814 A  12/1999  Gyorkos ..................... 514/18

OTHER PUBLICATIONS

Sumida, S. Agents Actions Suppl. (1982) AAS9 (Recent Prog. Kinins) 396–401.*

Taguchi et al., Curr. Clin. Pract. Ser. 65 (Cytoprotection and Cytobiology, vol. 10), 267–273 (1993).*

Oda et al. Japanese J. Pharmacology, 52 (1), 23–34 (1990).*

Dobosz et al. Mount Sinai Journal of Medicine, 59 (1), 43–46 (1992).*

Lefer et al. IRCS Med. Sci. : Libr. Compend. 8(5), 278 (1980).*

* cited by examiner

Primary Examiner—Karen Cochrane Carlson
Assistant Examiner—Chih-Min Kam
(74) Attorney, Agent, or Firm—Brown Martin Haller & McClain LLP

(57) ABSTRACT

Shock is a life threatening complication in situations associated with trauma including burns, surgery, ischemia, sepsis, and other critical care applications. Shock is induced by pancreatic proteases when they are released into the small intestine when the tissue is compromised due to trauma. Administration of protease inhibitors into the small intestine, either orally, intraveneously, or by direct lavage, was demonstrated to prevent shock in rats as determined by both survival time and molecular and histological analysis.

15 Claims, No Drawings

METHOD FOR TREATMENT AND PREVENTION OF PHYSIOLOGICAL SHOCK

CROSS-REFERENCES TO RELATED APPLICATIONS

This application claims the benefit of priority of U.S. provisional application Serial No. 60/167,311 filed Nov. 24, 1999 which is incorporated herein by reference in its entirety.

GOVERNMENT INTERESTS

This invention was made with government support under contract numbers AI41670 and HL43026 by the National Institutes of Health. The government has certain rights in the invention.

FIELD OF THE INVENTION

The present invention is a method for the prevention and treatment physiologic shock involving the inhibition or removal of proteases in the small intestine and in circulation to prevent the generation of the mediators of shock. It is also a method for the identification of the proteases involved in shock to allow for the development of protease inhibitors for use in the treatment of shock.

BACKGROUND OF THE INVENTION

Shock is a life-threatening complication in situations associated with trauma including burns, surgery, ischemia, sepsis, and other critical care applications. Shock is a broad term that describes a group of circulatory syndromes, all of which result in general cellular hypoxia. This leads to a depletion of the adenosine triphosphate (ATP), the failure of the sodium-potassium pump, mitochondrial dysfunction, and ultimately the release of a variety of toxic substances, including superoxides. Superoxides are toxic to essentially all tissues. They react with proteins and cause unfolding and are able to induce DNA damage. Additionally, cellular activation in the circulation can be detected by leukocytes or endothelial cells resulting in superoxide production, pseudopod projections, enzyme release, cytokine release, and expression of membrane adhesion molecules. Cell activation fundamentally alters the biomechanics of microvascular blood flow by a shift in rheological, adhesive, and cytotoxic cell properties. Eventually these stress responses give rise to irreversible cardiovascular collapse because of their combined effects on the microcirculation.

The interaction between activated leukocytes, both neutrophils and monocytes, and endothelial cells leads to accumulation of leukocytes in various organs, leading to cytotoxicity and cell death. Although such processes are mediated by humoral activators in the plasma of systemic circulation, an inflammation in organs throughout the body may eventually lead to multi-organ failure. When leukocytes are activated, neutrophil pseudopod formation is upregulated and several membrane adhesion molecules are expressed. This process lowers cell deformability and leads to accumulation of neutrophils in microcirculation. Not only may leukocytes start inflammation, but the abnormal cellular entrapment in the microcirculation also leads to immune suppression because of the reduced numbers of circulating cells.

Shock is a multifaceted systemic response to any of a number of stress inducing stimuli that results in cellular activation and release of a number of interacting response mediators, including cytokines, inflammatory and immune mediators, and nitric oxide (NO). During an immune response, oxygen free radicals and superoxides are generated to kill pathogens. However, oxygen free radicals and superoxides are also damaging to the host cells, resulting in oxidation of lipids, proteins and nucleic acids. The mediators of shock orchestrate complex biological interactions and amplification of signals that result in a systemic response to a localized insult.

Due to the multifaceted nature of factors inducing shock, development of therapeutics has been difficult. Most therapies have focused on the modulation of a single factor (e.g. cytokines, NO, endotoxin) to mitigate the effects of shock. Unfortunately, inhibition of any one of these pleiotropic factors is ineffective. Organ specific therapies can support life, but are not an ideal option as they often sacrifice remote organ function.

One potential therapeutic molecule that has been suggested for use in shock is bacterial/permeability-increasing protein (BPI), a protein involved in the immune response (Ammons, U.S. Pat. No. 6,017,881). Intestinal ischemia, frequently associated with shock, results in the breakdown of the intestinal mucosal permeability barrier allowing for the translocation of bacteria and/or endotoxin from the intestinal lumen to the vascular system. During shock, endotoxin has been detected in the portal vein, but its role in shock has not been clearly defined. BPI is a protein isolated from granules of mammalian polymorphonuclear cells (PMNs). PMNs are blood cells involved in the defense of the body against invading microorganisms. BPI is highly specific for gram negative bacteria and seems to have no deleterious effects on other pathogens or host cells. Administration of BPI to rats results in a decrease in the adverse physiological effects of intestinal ischemia which may catalyze the other symptoms of shock. However BPI only effects one of the pathways that are activated in shock, so it is of limited use. Additionally, BPI acts by attacking the endotoxin and bacteria afterthey have been released from the intestine into the bloodstream; therefore, it can not be used to prevent the occurrence shock.

There are no satisfactory drugs, treatment methods, or interventions available for the prevention of shock. All currently available methods for the treatment of shock deal with the symptoms, rather than the cause. For this reason, current clinical approaches are limited in their efficacy and can only prevent further damage from occurring.

SUMMARY OF THE INVENTION

Until the initiators, rather than the downstream mediators, of shock are identified, it will not be possible to develop satisfactory methods to prevent or treat shock. The present invention is the discovery of a role for proteases, from the pancreas, circulating cells, and other tissues, as the initiators of shock. During a normal immune response, proteases are generated by a number of circulating cells with no systemic ill effects. However during shock, there is a n overactivation of the immune system resulting in an overproduction of proteases. Similarly under normal circumstances after eating, pancreatic digestive enzymes are released into the small intestine after eating with no adverse effects. However, during shock, the intestinal permeability barrier of the small intestine is compromised, revealing protease susceptible sites not present under normal conditions. This "self-digestion" process produces a variety of protease digestion products that are responsible for shock. Such digestion products may include lipid, carbohydrate or other components from post-translational modifications. Therefore, shock is most effectively treated by the inhibition or elimination of the proteases that generate the activators of shock. Ideally by preventing the activation of the proteases by inhibiting the conversion of the proenzyme to the enzyme.

The present invention is also a method for the prevention and treatment of shock involving the inhibition or elimination of proteases present in the lumen of the small intestine and in circulation during shock. Protease inhibition can be achieved prophylactically by administration of protease inhibitors to the subject before a known potential shock inducing event (e.g. cardiac surgery). Alternatively, in trauma situations, protease inhibitors can be introduced directly into the small intestine by lavage, inserted either endoscopically or directly into the intestine, to flush the proteases out of the intestine. Additionally, protease inhibitors could be administered intravenously in both situations to inhibit proteases in circulating cells and throughout the body. Any of a number of protease inhibitors could be used for the purpose of inhibiting or treating shock including any of the known plasma protease inhibitors (e.g. anti-trypsin, anti-chymotripsin, C1 inhibitor, antithrombin III, alpha-2-macroglobulin), non-toxic amino acid/peptide substrate analog inhibitors, and non-amino/peptide chemical analogs that bind to the active site of the protease and block function. Inhibitor selection is based on the desired route of administration, desired pharmacokinetic properties, interaction with other patient medications, and other issues known to one skilled in the art.

The present invention is also a method for identifying the proteases that are involved in shock to allow for the development of protease inhibitors that are specific to those activated in shock. An ideal protease would inhibit the activation of the pro-form of the shock mediating proteases without inhibiting the activation of the proteases involved in other essential processes (e.g. blood clotting).

DETAILED DESCRIPTION AND PREFERRED EMBODIMENTS

Since the initiating factors of shock are released early (<1 hour) after the initiation of shock and may not require de novo protein synthesis, homogenates were prepared from several organs to identify these initiating factors. Homogenates were tested for their ability to activate neutrophils, a hallmark of shock. Male Wistar rats (250–350 gm) were housed in a controlled environment and maintained on a standard pellet diet for at least three days before the experiments. Access to food was maintained until anesthesia to preserve pancreatic discharge. After general anesthesia (pentobarbital, 50 mg/kg i.m.), the femoral arteries and veins were cannulated. A central incision was made and the heart, liver, spleen, small intestine, kidney, adrenal gland and pancreas were harvested.

The organs were immediately washed in cold 0.25 M sucrose solution, homogenized in Krebs-Henseleit solution (1:3 w/v), and the homogenate was diluted (1:2 v/v Krebs-Henseleit), following the protocol established by Glen and Lefer (*Circ. Res.*, 1971). This homogenate served as the stock solution for all experiments. Aliquots were heated for 2.5 hours at 38° C. with mild stirring and the supernatant collected after centrifugation at 500 g for 10 min. Incubation of tissue homogenates at 38° C. promotes enzymatic activity and enhances production of the cellular activation factors.

It was expected that initiators of shock would also be present in the circulation during shock. Therefore, shock was induced in rats by occlusion of the splanchnic artery to cause intestinal ischemia. Blood was collected from the portal vein and the plasma was isolated for subsequent experimentation.

Neutrophils were isolated from venous blood collected from healthy human volunteers in heparinized vacutainer tubes and stored at 4° C. Human neutrophils (PMNs) were used in these studies after it was shown in pilot studies that the rat organ extracts stimulated activation of both human and rat neutrophils to a similar degree. Human neutrophils can be gathered in larger numbers and are more readily isolated than rat neutrophils, which significantly overlap with a subpopulation of rat erythrocytes during isolation.

Neutrophil isolation was carried out using gravity sedimentation to remove erythrocytes and centrifugation through a Percoll gradient. Isolated neutrophils were resuspended in PBS to achieve a count of $10^6$ neutrophils/ml. 100 $\mu$l aliquots of suspended neutrophils were added to 100 $\mu$l of activating agent (e.g. tissue homogenate) or PBS as a control, and incubated for 10 minutes at 27° C. After incubation, 100 $\mu$l of 3% glutaraldehyde (Fisher Scientific, Fair Lawn, N.J.) was added to fix the cells. 100 $\mu$l of crystal violet in phosphate (pH: 7.4) buffer was added to label leukocyte nuclei for identification on wet mount preparations. Freely suspended neutrophils with pseudopodia were identified by their segmented nuclei and by the presence of cytoplasmic granules. One hundred neutrophils were counted per slide. Cells having pseudopod projections greater than about 1 $\mu$m were considered positive. Repeated measurements by the same investigator indicated that such counts were reproducible within 2%.

Another aspect of neutrophil activation is superoxide production and free radical formation. The damaging effects of active oxygen species can be mitigated by a number of antioxidants. Antioxidants function both by inhibiting the production of activated oxygen species (e.g. superoxide dismutase, catalase) and free radical scavengers (e.g. vitamins C and E and glutathione). NBT reduction to blue-black formazan crystals by neutrophils is associated with superoxide production. Fresh arterial blood (0.1 ml) from healthy donor rats was mixed with 25 $\mu$l of stock homogenate solution and immediately transferred into a clean siliconized 1 dram glass vial (Sigma Diagnostics, St. Louis, Mo.), then mixed with an equal volume of 0.1% NBT-solution. The glass vials were incubated at 37° C. in air for 10 minutes and subsequently allowed to stand at room temperature for an additional 10 minutes. At the end of this period, the blood-NBT mixture was gently stirred. Coverslip smears were made and stained with Wright's stain. A total of 100 neutrophils were counted at 100× oil objective magnification. Neutrophils that showed a stippled cytoplasm with deposits of formazan or a dense clump of formazan were counted as NBT-positive cells. Slides were measured in duplicate or triplicate and the results were averaged. Superoxide production was stimulated significantly by liver homogenates (21±3%) as compared to buffer controls (7%±2%, $p<0.05$), but this stimulation was much weaker than that seen by pancreatic homogenates (42%±14%, $p<0.005$).

Free radical formation was confirmed by an alternative chemiluminescence technique. Human venous blood from healthy volunteers was collected in heparinized vacutainer tubes and centrifuged for 10 minutes at 500 g. The plasma layer, including the buffy coat, was carefully collected using a sterile transfer pipette. 3 ml of plasma were mixed with lucigenin (N,N'-dimethyl-9,9'-bisacridinium dinitrite) (Sigma). 1 ml of a 1 mM stock solution of lucigenin in saline, final concentration of 200 $\mu$M, which is near the optimal concentration, was used for each measurement performed in small petri dishes (60 mm diameter). Plasma was diluted with saline to achieve a count of $1.2\times10^5$ neutrophils/ml. 1 ml of either whole pancreatic homogenate, or PBS as a control, was added to the plasma. The photons emitted from the chemiluminescence were counted for 120 minutes with a photomultiplier (Stanford Research 4000, Sunnyvale, Calif.) in a light-shielded housing. Again, highly significant levels of superoxide production were only seen with the pancreatic homogenates.

Pancreatic homogenates were found to contain neutrophil activators, indicating that potential mediators of shock were generated. Other tissue homogenates were found to have effects comparable to buffer controls in most situations. Plasma from the shocked rats induced activation of neutrophils, whereas normal plasma did not.

To determine if pancreatic homogenates could induce a "systemic response" in vitro, non-pancreatic tissues were incubated with substimulatory quantities of pancreatic homogenate (100 $\mu$l pancreatic homogenate/3 ml organ homogenate). This resulted in significantly elevated levels of neutrophil activation by non-pancreatic homogenates, particularly intestine. As the pancreas produces a number of digestive enzymes, including proteases, a cocktail of trypsin and chymotrypsin was added to non-pancreatic tissue and the neutrophil activation assays were performed. Protease treated cell homogenates were found to activate neutrophils, despite the fact that the proteases alone were unable to stimulate neutrophil activation, suggesting that the proteolytic products were the mediators of shock. Homogenization of the pancreas in the presence of protease inhibitors, including phenylmethylsulfonylfluoride (PMSF, Sigma Chemicals, St. Louis, Mo.), 6-amidino-2napthyl p-guanidobenzoate dimethane-sulfate (ANGD, nafamostat mesilate, Futhan, Torii Pharmaceutical, Chiba, Japan) and gabaxalate mesilate (FOY, Ono Pharmaceutical, Japan), all serine protease inhibitors, significantly decreased the ability of the homogenate to stimulate neutrophil activation. A decrease from 59±10% to 9±12% was observed for ANGD treated extracts. Addition of protease inhibitors to the homogenate after preparation did not significantly decrease neutrophil activation by the extract (52±34%). This clearly demonstrates that it is the proteolytic products rather than the proteases that mediate shock. Addtionally it demonstrates that a variety of tissues may be activated to generate shock mediators upon exposure to proteases.

Pancreatic homogenates were found to be potent activators of shock in vivo. Rats were cannulated via the femoral arteries and veins under general anesthesia (pentobarbital, 50 mg/kg i.m.) and saline, without or with ANGD, was infused to examine the response of the circulation after administration of pancreatic homogenate. The arterial catheter served to record mean arterial pressure (MAP) and heart rate. The venous catheter was connected to an infusion pump (Model 355, Sage Instruments, Orion Research, Inc., Cambridge, Mass.) to continuously inject either the protease inhibitor ANGD (3.3 mg/kg body wt per hour) or a comparable volume of saline. No heparin was injected other than that needed to maintain open catheters (10 U/ml Plasma-Lyte, Travenol Laboratory Inc., Deerfield, Ill.). After a one hour pretreatment, a bolus injection of filtered (0.78 $\mu$m vacuum filter, Millipore) stock pancreatic homogenate was administered (2 ml). The extent to which pancreatic homogenate induced hypotension and circulatory shock, both in the presence and absence of ANGD, was examined.

Injection of pancreatic homogenates into rats resulted in immediate and irreversible circulatory collapse, typically within 6 minutes. Shock was inhibited by a one hour pretreatment with the protease inhibitor ANGD delivered by an infusion pump into a venous catheter. MAP and heart rate returned to normal levels within 20 minutes in the ANGD pre-treated animals, and none of these animals died within the 60 minute post-injection observation period. This indicated that pretreatment of a subject with on/yprotease inhibitors can prevent shock after injection of pancreatic homogenates.

Protease inhibitors prevented shock when applied directly into the lumen of the intestine as well. The small intestine of rats was perfused at a constant flow rate (4.0 ml/min) with 45 ml of rat intestinal fluid supplemented with 5 ml of 5% glucose (IF) or 50 ml of saline with 0.1% glucose (SAL) or with ANDG at a final concentration of 0.2 mg/ml. The perfusate was recirculated continuously throughout the entire procedure. After 15 min of intestinal perfusion, the animals were subjected to 100 min. of splanchnic ischemia, which was confirmed by cyanotic organ discoloration and loss of the pressure pulsation in the mesentery. After 100 min of splanchnic ischemia, the celiac and superior mesenteric arteries were reperfused.

The process of shock was monitored by a number of methods in various tissues throughout the body. Intestinal fluid was analyzed for serine protease activity. One milliliter of circulating fluid in the intestine was collected from the reservoir before ischemia and 90 min after ischemia. Perfusion of the lumen of the intestine with saline, either without or with the protease inhibitor, significantly decreased the serine protease activity level in the intestine before ischemia (IF=$5.8\pm1.8\times10^3$ units/ml vs. SAL=$2.0\pm0.9\times10^3$ units/ml and ANGD=$1.2\pm0.1\times10^3$ units/ml). After 90 min of ischemia, the serine protease activity levels in the IF, SAL, and ANGD groups were $5.6\pm2.3\times10^3$ units/ml, $3.3\pm2.3\times10^3$ units/ml, and $1.2\pm0.2\times10^3$ units/ml, respectively. Intestinal perfusion with ANGD kept the serine protease activity lower than in the other two groups ($p<0.05$, SAL vs. ANGD; $p<0.01$ ANGD vs. IF and SAL groups).

Arterial and portal venous blood (0.3 ml each) were sampled before ischemia, after 90 min of ischemia, and 30, 60, and 120 min postreperfusion. The samples were analyzed for leukocyte count and activation based on crystal violet staining. In the preischemic period, the leukocyte counts were the same in all three groups. In the IF And SAL groups, the leukocyte count in arterial blood started to decrease after ischemia and reached its lowest value 120 min after reperfusion. Intestinal perfusion of the protease inhibitor completely ameliorated leukopenia. Similarly, ANGD was able to inhibit the activation of circulating neutrophils (15.0±1.6%) as compared to both IF (23.3±1.0%, $p<0.05$) and SAL (25.0±1.6%, $p<0.05$) at 120 minutes postperfusion.

Myeloperoxidase activity was used as a marker for assessment of leukocyte infiltration into the small intestine, liver, and lung. Tissue myeloperoxidase levels were determined by a spectrophotometric method. At 120 minutes of reperfusion, myeloperoxidase levels were increased in intestine (36.1±3.9 U/g to 309.3±51.0 U/g), liver (0.4±0.1 U/g to 2.6±0.3 U/g), and lung (29.0±4.4 U/g to 199.2±33.9 U/g). This is an early indicator of leukocyte infiltration and organ failure in shock. Intestinal perfusion in the lumen of the intestine with ANGD, however, significantly attenuated myloperoxidase activity in intestine (62.5±19.8 U/g), liver (1.0±0.1 U/g), and lung (87.0±13.4 U/g).

Thickness of the intestinal mucosa was used as an indicator of damage to the intestine. A sample of small intestine was longitudinally dissected, fixed in 10% buffered formalin, and embedded in paraffin. Five-micrometer sections were made and stained with hematoxylin and eosin and examined at 200× magnification. Severity of intestinal injury was estimated by the length between the tip of the villi and the musculus mucosae, a measure of mucosal layer thickness. In each specimen, the measurement was made at 10 randomly selected locations and averaged. Intestinal perfusion of protease inhibitor served to maintain mucosal thickness and to reduce intestinal injury (IF 252.0±34.0 $\mu$M vs ANGD 378.0±38.0 $\mu$M).

The level of edematous lung injury was assayed by a pulmonary wet/dry ratio. Lung lobes were harvested, wet weight was determined and samples were dried at 70° C. for 72 hours. The dried tissue was weighed, and the ratio of wet to dried weight was calculated. Edema was much greater in the IF (5.65±0.33) and SAL (4.88±0.39) groups as compared to the ANGD (3.66±0.27) group which was similar to non-shock controls.

These studies clearly indicate the role of pancreatic proteases in shock and the protective effects of protease inhibitors. Pancreatic enzymes are released normally into the small intestine for digestion with no adverse effects. However, during shock, the intestinal permeability barrier is compromised. This can reveal protease susceptible sites not present under normal conditions. Similar sites are revealed upon homogenization of the intestine. Tissues are broken down and proteolytic products that are strong activators of shock are released. Clearly a variety of proteolytic products can act as mediators of shock as a variety of tissue homogenates can be activated with pancreatic extract or proteases to activate neutrophils. Therefore, shock is most effectively treated by preventing protease activation or by the inhibition or elimination of the proteases that generate the activators of shock.

The preferred embodiments of the invention are described below. All publications mentioned herein are incorporated herein by reference to illustrate known methods and/or materials which may be of use in, but not essential to, the practice of the invention.

EXAMPLE 1

Prophylactic treatment for the prevention of shock during cardiac surgery. One to eight hours prior to surgery, preferably four hours prior to surgery, ANGD is administered orally at a dose of 0.1 to 1.0 mg/kg/hr, preferably 0.3–0.5 mg/kg/hr to a fasting patient to inhibit pancreatic proteases in the intestine. Fasting additionally decreases the production of pancreatic digestive enzymes. Prior to surgery, ANDG is administered by IV drip 0.1–1.0 mg/kg/hr, preferably 0.3–0.5 mg/kg/hr. As many cardiac patients suffer from inflammation, which results in the production of superoxides which are involved in making shock systemic, the IV may be supplemented with antioxidants. Antioxidants, including glutathione, catalase, and superoxide dismutase inactivate superoxides present in the blood before surgery and raise the threshold of the level that would need to be produced to induce shock. IV nutrients are administered for 6–24 hours, preferably 8–12 hours postoperatively to allow for clearance of the protease inhibitors from the digestive tract.

EXAMPLE 2

Intestinal lavage for the prevention of shock during abdominal surgery. Prior to surgery, the large intestine of a fasting patient is cleared by administration of an enema and/or laxative. As soon as is practical after the administration of anesthesia, a catheter is inserted directly into the intestine, between the stomach and the proximal duodenum. The intestine is flushed with a saline solution supplemented with glutathione and 0.5 to 5.0 mg/kg/hr FOY, preferably 1.5 to 2.5 mg/kg/hr at a flow rate of 50 to 200 ml/min, preferably 100 ml/min for at least 5 minutes prior to the subsequent surgical procedures and is continued throughout the procedure at a similar rate. IV nutrients are administered for 6–24 hours, preferably 8–12 hours postoperatively to allow for clearance of the protease inhibitors from the digestive tract.

EXAMPLE 3

Intestinal ravage for treatment of shock in victims of trauma. A patient is admitted to a trauma unit with severe injuries. As soon as is practical after the administration of anesthesia, a catheter is inserted endoscopically into the intestine, proximal to the duodenum. The intestine is flushed with a saline solution supplemented with an effective dose of a combination of ANGD and FOY at a flow rate of 0.5 to 2 liters/min, preferably 1 liter/min for 20 minutes to clear the intestine. Subsequently the flow rate is decreased to 0.02 to 0.5 liters/min, preferably 0.1 liters/min for the duration of potentially traumatic events. IV nutrients are administered for 6–24 hours, preferably 8–12 hours postoperatively to allow for clearance of the protease inhibitors from the digestive tract.

EXAMPLE 4

Intravenous infusion for the prevention of shock in victims of trauma. At the site of an accident, victims are treated by emergency medical technicians. Intravenous infusion of a therapeutic dose of $\alpha$-2 macroglobulin (0.1–10 mg/kg/hr) may be combined with saline containing other desired therapeutics including antioxidants and analgesics. An initial bolus of $\alpha$-2 macroglobulin may be given. Infusion with $\alpha$-2 macroglobulin is continued until the patient is stabilized. In the case of suspected intestinal or pancreatic injury, protease inhibitors are administered via an esophageal tube directly into the stomach, 1–10 mg/kg initial dose.

EXAMPLE 5

Combination of oral prophylaxis and intestinal lavage for the prevention ofshockduringsurgery. Methods of protease inhibitor administration can be combined to save time at the beginning of surgery or to maintain levels of intestinal inhibitors during longer surgeries. Anti-trypsin is administered orally preferably at a dose of 0.1 to 10 mg/kg/hr to the patient one to eight hours, preferably four hours before surgery. As soon as is practical after the administration of anesthesia, a catheter is inserted endoscopically into the intestine, at the junction between the stomach and the proximal duodenum. The intestine is flushed with a saline solution supplemented with a therapeutic dose of anti-trypsin/chymotrypsin, preferably at a flow rate of 0.1 to 10 mg/ml/hr, and then throughout the surgical procedure at a flow rate 0.02 to 0.5 liters/min, preferably 0.1 liters/min. IV nutrients are administered for 6–24 hours, preferably 8–12 hours postoperatively to allow for clearance of the protease inhibitors from the digestive tract.

EXAMPLE 6

Development of protease inhibitors for the treatment of shock. Proteases involved in the production of shock mediators are present in pancreatic extracts. The proteases can be identified and isolated by any of a number of methods well known to those skilled in the art (e.g. column chromatography, differential centrifugation, gel electrophoresis). Using combinatorial chemistry, structural modeling or other methods, a panel of protease inhibitors can be generated and tested for affinity and specificity for the shock proteases. Protease inhibitors may also be selected based on other criteria including pharmacokinetic and pharmacodynamic properties, drug interactions and side effects.

Although an exemplary embodiment of the invention has been described above by way of example only, it will be understood by those skilled in the field that modifications may be made to the disclosed embodiment without departing from the scope of the invention, which is defined by the appended claims.

We claim:

1. A method for prevention or treatment of physiological shock comprising administering to an individual containing an intestine a therapeutic dose of a serine protease inhibitor directly into the small intestine to inactivate a protease, thereby ameliorating shock.

2. The method as in claim 1, wherein the protease is a pancreatic protease.

3. The method as in claim 1, wherein the protease is generated by circulating cells.

4. The method as in claim 1, wherein the serine protease inhibitor is additionally administered orally.

5. The method as in claim 1, wherein the serine protease inhibitor is additionally administered intravenously.

6. The method as in claim 1, wherein the serine protease inhibitor is a natural plasma protease inhibitor.

7. The method as in claim 1, wherein the serine protease inhibitor is 6-amidino-2-naphthyl p-guanidinobenzoate dimethane sulfonate (ANDG).

8. The method as in claim 1, wherein the serine protease inhibitor is gabexate mesilate (FOY).

9. The method as in claim 1, wherein antioxidants are administered in conjunction with the serine protease inhibitor.

10. The method as in claim 9, wherein the antioxidants are administered orally.

11. The method as in claim 9, wherein the antioxidants are administered intravenously.

12. The method as in claim 9, wherein the antioxidants are administered by lavage into the intestine.

13. The method as in claim 9, wherein the antioxidant is an inhibitor of the production of active oxygen species.

14. The method as in claim 9, wherein the antioxidant is a free radical scavenger.

15. The method as in claim 14, wherein the antioxidant is glutathione.

* * * * *

UNITED STATES PATENT AND TRADEMARK OFFICE
CERTIFICATE OF CORRECTION

PATENT NO.    : 6,534,283 B1
DATED         : March 18, 2003
INVENTOR(S)   : Schmid-Schoenbein et al.

It is certified that error appears in the above-identified patent and that said Letters Patent is hereby corrected as shown below:

<u>Title page,</u>
Item [73], Assignees, please change "The Scripps Institute" to -- The Scripps Research Institute --.

Signed and Sealed this

Twelfth Day of August, 2003

JAMES E. ROGAN
*Director of the United States Patent and Trademark Office*